United States Patent [19]

Rohde, Jr. et al.

[11] Patent Number: 5,445,957
[45] Date of Patent: Aug. 29, 1995

[54] ENZYME FOOD SUPPLEMENT COMPOSITION CONTAINING BETA-FRUCTOFURANOSIDASE, CELLULASE AND HEMICELLULASE

[75] Inventors: Rodger R. Rohde, Jr., Wayne, N.J.;
Edward F. Schuler, Keswick, Va.;
Richard A. Handel, Ridgewood, N.J.

[73] Assignee: Triarco Industries, Inc., Paterson, N.J.

[21] Appl. No.: 352,703

[22] Filed: Dec. 5, 1994

Related U.S. Application Data

[62] Division of Ser. No. 194,712, Feb. 10, 1994, abandoned.

[51] Int. Cl.$^6$ .................. C12N 9/24; C12N 9/42; C12N 9/20; C12N 9/62
[52] U.S. Cl. ................... 435/200; 435/209; 435/198; 435/219; 435/225; 435/99; 424/94.2; 424/94.61; 424/94.6; 424/551
[58] Field of Search ............... 435/200, 209, 198, 219, 435/225, 99; 424/94.2, 94.61, 94.6, 551

[56] References Cited

U.S. PATENT DOCUMENTS

| | | | |
|---|---|---|---|
| 3,632,346 | 1/1972 | Sherba et al. | 426/46 |
| 3,846,239 | 11/1974 | Delente et al. | 435/208 |
| 4,008,334 | 2/1977 | Hansen | 426/46 |
| 4,079,125 | 3/1978 | Sipos | 424/32 |
| 4,216,235 | 8/1980 | Dasek et al. | 426/456 |
| 4,376,127 | 3/1983 | Lunde | 426/46 |
| 4,431,737 | 2/1984 | Olivieri et al. | 435/208 |
| 4,447,412 | 5/1984 | Bilton | 424/16 |
| 4,695,457 | 9/1987 | Hellgren et al. | 424/94 |
| 5,013,557 | 5/1991 | Tai | 424/493 |
| 5,137,818 | 8/1992 | Harder et al. | 435/177 |
| 5,240,967 | 8/1993 | Nakatsu et al. | 514/570 |
| 5,260,074 | 11/1993 | Sipos | 424/497 |
| 5,314,814 | 5/1994 | Harder et al. | 435/177 |

FOREIGN PATENT DOCUMENTS

| | | |
|---|---|---|
| 341885 | 11/1989 | European Pat. Off. . |
| 1107824 | 3/1968 | United Kingdom . |
| WO90/14101 | 11/1990 | WIPO . |

OTHER PUBLICATIONS

Amano Enzymes Technical Bulletin No. CEZ-1, "Cellulase AP 'Amano' (Cellulolytic Enzyme Preparation)" (1977).
Cellulase-BCL, Bio-Cat, Ic. (Undated.
Cellulase-BC, Bio-Cat, Inc. (1992).

(List continued on next page.)

*Primary Examiner*—David M. Naff
*Assistant Examiner*—Michael V. Meller
*Attorney, Agent, or Firm*—Fitzpatrick, Cella, Harper & Scinto

[57] ABSTRACT

This invention relates to a beta-fructofuranosidase enzyme food supplement composition, which alleviates gastrointestinal distress caused by ingested food containing oligosaccharides, comprising a beta-fructofuranosidase enzyme, a cellulase enzyme and a hemicellulase enzyme. More particularly, the enzyme food supplement composition of this invention comprises a beta-fructofuranosidase enzyme, a cellulase enzyme, a hemicellulase enzyme, a lipase enzyme and an acid protease enzyme. This invention also relates to a method of alleviating gastrointestinal distress in the gastrointestinal system of a human being, which distress is caused by ingested food containing oligosaccharides, the method comprising the step of ingesting a beta-fructofuranosidase enzyme food supplement composition comprising a beta-fructofuranosidase enzyme, a cellulase enzyme and a hemicellulase enzyme, to convert oligosaccharides contained in the ingested food to reducing sugars. More particularly, the method of alleviating gastrointestinal distress of this invention comprises the step of ingesting an enzyme food supplement composition comprising a beta-fructofuranosidase enzyme, a cellulase enzyme, a hemicellulase enzyme, a lipase enzyme and an acid protease enzyme, to convert oligosaccharides contained in the ingested food to reducing sugars.

10 Claims, No Drawings

OTHER PUBLICATIONS

Amano Enzymes, Technical Bulletin No. CEZ-3, "Hemi-Cellulase 'Amano' (Cellulolytic Enzyme Preparation)" (1977).

Hemicellulase-BC, Bio-Cat, Inc. (Undated).

Xylanase-BC, Bio-Cat, Inc. (Undated).

Legumase L Product Data Sheet, TRIARCO Industries, Inc. (1992).

Novozym 230 Specification Sheet, Novo Nordisk Bioindustrials, Inc. (1992).

Legumase Product Data Sheet, Triarco Industries, Inc. (1992).

Enzyme Additive For Beans Reduces Gassy Feeling (1991).

Source Book of Food Enzymology, Enzymes as Health and Safety Benefits, pp. 653–654, 1981.

Merck Index, 10th Edition (1983) p. 487 Item 4873 "Invertase".

Slominski, J. Sci. Food Agric., 1994, 65, 323–330.

ENZYME FOOD SUPPLEMENT COMPOSITION CONTAINING BETA-FRUCTOFURANOSIDASE, CELLULASE AND HEMICELLULASE

This application is a division of application Ser. No. 08/194,712, filed Feb. 10, 1994, now abandoned.

FIELD OF THE INVENTION

This invention relates to a beta-fructofuranosidase enzyme food supplement composition, which alleviates gastrointestinal distress caused by ingested food containing the oligosaccharides raffinose, stachyose and verbascose. In one embodiment, the enzyme food supplement composition of this invention comprises a beta-fructofuranosidase enzyme, a cellulase enzyme and a hemicellulase enzyme. More particularly, the beta-fructofuranosidase enzyme food supplement composition of this invention comprises a beta-fructofuranosidase enzyme, a cellulase enzyme, a hemicellulase enzyme, a lipase enzyme and an acid protease enzyme.

This invention also relates to a method of alleviating gastrointestinal distress in the gastrointestinal system of a human being, which distress is caused by ingested food containing the oligosaccharides raffinose, stachyose and verbascose. In one embodiment, the method of this invention comprises the step of ingesting a beta-fructofuranosidase enzyme food supplement composition comprising a beta-fructofuranosidase enzyme, a cellulase enzyme and a hemicellulase enzyme, to convert the oligosaccharides raffinose, stachyose and verbascose contained in ingested food to reducing sugars. The beta-fructofuranosidase enzyme converts these oligosaccharides, which cause gastrointestinal distress, to reducing sugars which are easily digested by the endogenous enzymes in the gastrointestinal system. More particularly, the method of alleviating gastrointestinal distress of this invention comprises the step of ingesting a beta-fructofuranosidase enzyme food supplement composition comprising a beta-fructofuranosidase enzyme, a cellulase enzyme, a hemicellulase enzyme, a lipase enzyme and an acid protease enzyme, to convert the oligosaccharides raffinose, stachyose and verbascose contained in ingested food to reducing sugars.

BACKGROUND OF THE INVENTION

The subject beta-fructofuranosidase enzyme food supplement composition was invented to meet the needs of the numerous people who needlessly suffer from gastrointestinal discomfort and flatulence because of the difficulty they have in digesting the oligosaccharides raffinose, stachyose and verbascose, which are known as alpha-galactosyl oligosaccharides, and are present in various foods such as legumes, bran, cruciferous vegetables, onions, garlic and some fruits. Because these oligosaccharides are not digestible by enzymes endogenous to a human's gastrointestinal system, they pass intact to the large intestine, where they are consumed by putrefactive bacteria such as Clostridia and E. coli and evolve as the metabolic by-product gases carbon dioxide and hydrogen as well as noxious methane. Even though the percentage of the oligosaccharides raffinose, stachyose and verbascose in these types of foods may seem small (for example, approximately only two percent are found in a prime offender, refried beans), waste gases can still be produced in sufficient volumes to cause gastrointestinal cramping and discomfort, as well as flatulence, that often accompany the intake of ingested foods containing these oligosaccharides. The beta-fructofuranosidase enzyme of the present invention is able to convert these offending oligosaccharides into the simpler, digestible sugars, such as fructose, which are known as reducing sugars, thereby alleviating gastrointestinal distress.

Prior to the present invention, to alleviate the gastrointestinal problems caused by ingesting foods containing these offending oligosaccharides people had the choice of either avoiding these foods entirely or using a food additive or an enzyme food supplement composition which contained the enzyme alpha-galactosidase as the only active ingredient.

A liquid product sold under the trademark BEANO by AkPharma has been described as an enzyme or food additive that reduces or eliminates the intestinal gas produced when foods such as beans, broccoli, bran and other vegetables and grains that are a staple in healthy low-fat, high-fiber diets, are eaten. That liquid food additive BEANO product contains the enzyme alpha-galactosidase obtained from *Aspergillus niger*. The alpha-galactosidase enzyme contained in the BEANO product works in a different manner than the beta-fructofuranosidase enzyme contained in the enzyme food supplement composition of the present invention. The beta-fructofuranosidase enzyme reduces the oligosaccharides of raffinose, stachyose and verboscose by converting the fructofuranose portion of the molecule to fructose. The alpha-galactosidase enzyme reacts with the galactopyranose portion of the raffinose, stachyose and verbascose molecules, but leaves the glucopyranose frustofuranose portion of those molecules intact.

The additional enzymes contained in the compositions of the present invention—the cellulase, hemicellulase, lipase and acid protease enzymes—are believed to contribute to the further alleviation of gastrointestinal distress by enhancing the conversion of oligosaccharides to reducing sugars in the following manner.

The cellulase and hemicellulase enzymes of the enzyme food supplement compositions of this invention degrade the cellulosic and hemicellulosic constituents contained in the plant cell walls of the ingested food. This degradation leads to the release of oligosaccharides contained in the plant cells, thereby making these oligosaccharides available for conversion to reducing sugars by the beta-fructofuranosidase enzyme of the present invention. Without the presence of the cellulase and hemicellulase enzymes in the enzyme food supplement composition of the present invention, the plant cell walls contained in ingested food would not be degraded by the digestive enzymes endogenous to the gastrointestinal tract of a human being. The cellulase enzyme is important because it degrades the primary plant cell wall, which if passed to the colon as intact plant cells can be attacked by putrefactive bacteria such a *C. perfringens*, which ferment the contents of the plant cell, causing gastric distress. The hemicellulase enzyme is important because it breaks the structure of xylans and related compounds, which are usually associated with cellulose and lignin in leguminous foods. This enzymatic activity helps to free the cellulose for hydrolysis by cellulase. Therefore, the presence of the cellulase and hemicellulase enzymes of the enzyme food supplement compositions of this invention degrade cellulosic and hemicellulosic constituents contained in the ingested food, to attain an enhanced quantity of reducing sugars through oligosaccharide conversion, thereby further alleviating gastrointestinal distress.

The optional lipase enzyme is important because many recipes containing legumes, such as refried beans, also contain large amounts of fat, and the lipase enzyme aids in the digestion of fats or lipids. The maldigestion of such fats or lipids can cause or aggravate heartburn, hiatus hernia and esophageal reflux. Ingested lipids can also coat ingested food particles and limit their ability to interact with the other enzymes, in particular the beta-fructofuranosidase enzyme of the present invention. This coating effect is diminished by enzymatic hydrolysis of the fats or lipids contained in ingested foods.

The optional acid protease enzyme of the present invention is important for several reasons. The acid protease enzyme degrades proteinaceous trypsin inhibitor and alpha-amylase inhibitor, which interfere with normal digestion, in addition to aiding in general protein digestion. In addition, the acid protease enzyme of the present invention helps to break down lipoproteins and glycoproteins contained in foods like legumes.

Because foods containing the troublesome oligosaccharides raffinose, stachyose and verbascose also contain lipids and lipoproteins which tend to coat the ingested food and thereby hinder the beta-fructofuranosidase enzyme from contacting these oligosaccharides and thereby converting them to reducing sugars, an additional advantage of the present invention is the presence of a lipase enzyme to hydrolyze the ingested lipids coating ingested food and the presence of an acid protease enzyme to deconjugate the ingested lipoproteins coating ingested food, to attain an enhanced quantity of reducing sugars through oligosaccharide conversion.

The enzyme food supplement compositions of this invention are of value to any one who has suffered gastrointestinal distress caused by ingesting foods containing the oligosaccharides raffinose, stachyose and verbascose.

To the best of applicant's knowledge, the presently claimed beta-fructofuranosidase enzyme food supplement compositions are the first such compositions that seek to alleviate the problem of gastrointestinal distress by utilizing the unique combination of a beta-fructofuranosidase enzyme, a cellulase enzyme and a hemicellulase enzyme, and optionally a lipase enzyme and an acid protease enzyme.

The major advantage of the present invention is that the unique combination of enzymes is able to convert, effectively in the gastrointestinal system of a human being, undigestible oligosaccharides to digestible reducing sugars, thereby alleviating gastrointestinal distress which is normally associated with the ingestion of foods containing such oligosaccharides.

These and additional objects and advantages of the present invention are shown from the description below.

SUMMARY OF THE INVENTION

This invention relates to a beta-fructofuranosidase enzyme food supplement composition, which alleviates gastrointestinal distress caused by ingested food containing oligosaccharides, said composition comprising a beta-fructofuranosidase enzyme, a cellulase enzyme and a hemicellulase enzyme.

This invention further relates to a beta-fructofuranosidase enzyme food supplement composition, which alleviates gastrointestinal distress caused by ingested food containing oligosaccharides, said composition comprising a beta-fructofuranosidase enzyme, a cellulase enzyme, a hemicellulase enzyme, a lipase enzyme and an acid protease enzyme.

This invention still further relates to the above-mentioned beta-fructofuranosidase enzyme food supplement compositions wherein the beta-fructofuranosidase enzyme is obtained from *Saccharomyces cerevisiae*, the cellulase enzyme is obtained from a member selected from the group consisting of *Aspergillus niger* and *Trichoderma viride* (*reesei*), the hemicellulase enzyme is obtained from *Aspergillus niger*, the lipase enzyme is obtained from *Aspergillus niger*, and the acid protease enzyme is obtained from *Aspergillus niger* var. *macrosporus*. In a method of use embodiment, the present invention relates to a method of alleviating gastrointestinal distress in the gastrointestinal system of a human being, which distress is caused by ingested food containing oligosaccharides, said method comprising the step of ingesting a beta-fructofuranosidase enzyme food supplement composition comprising a beta-fructofuranosidase enzyme, a cellulase enzyme and a hemicellulase enzyme, to convert oligosaccharides contained in the ingested food to reducing sugars. The beta-fructofuranosidase enzyme of the enzyme food supplement composition converts the oligosaccharides to reducing sugars. The cellulase and hemicellulase enzymes of the enzyme food supplement composition degrade cellulosic and hemicellulosic constituents contained in the ingested food, to attain an enhanced quantity of reducing sugars through oligosaccharide conversion.

In another method of use embodiment, the present invention further relates to a method of alleviating gastrointestinal distress in the gastrointestinal system of a human being, which distress is caused by ingested food containing oligosaccharides, said method comprising the step of ingesting an enzyme food supplement composition comprising a beta-fructofuranosidase enzyme, a cellulase enzyme, a hemicellulase enzyme, a lipase enzyme and an acid protease enzyme, to convert oligosaccharides contained in the ingested food to reducing sugars. The beta-fructofuranosidase enzyme of the enzyme food supplement composition converts the oligosaccharides to reducing sugars. The cellulase and hemicellulase enzymes of the enzyme food supplement composition degrade cellulosic and hemicellulosic constituents contained in the ingested food, the lipase enzyme of the enzyme food supplement composition hydrolyzes ingested lipids coating the ingested food, and the acid protease enzyme of the enzyme food supplement composition deconjugates ingested lipoproteins coating the ingested food, to attain an enhanced quantity of reducing sugars through oligosaccharide conversion.

DETAILED DESCRIPTION OF THE INVENTION

The beta-fructofuranosidase enzyme food supplement composition in accordance with this invention includes a beta-fructofuranosidase enzyme, a cellulase enzyme and a hemicellulase enzyme.

A beta-fructofuranosidase enzyme is defined as an invertase enzyme which catalyses the hydrolysis of sucrose into fructose and glucose and is characterized by its ability to hydrolyze raffinose. Since sucrose is both a beta-fructofuranoside and an alpha-glucoside, it is important to note that the beta-fructofuranosidase enzyme attacks the sucrose molecule from the fructose, not the glucose, end of the molecule. Beta-fructofuranosidase enzymes are generally obtained from yeast, and a particularly preferred beta-fructofuranosidase enzyme is obtained from *Saccharomyces cerevisiae*. Although the beta-fructofuranosidase enzyme can be obtained by culturing the *Saccharomyces Cerevisiae* organism, then extracting and purifying the enzyme by known and conventional techniques, the applicant has found it more efficient to purchase the enzyme from any one of the following sources: Bio-Cat, Inc., Industrial Drive, Louisa, Va. 23093; Amano International Enzyme Company, Inc., 250 East Zion Crossroads, Troy, Va. 22974. The invention is not, however, to be limited by the source of the beta-fructofuranosidase enzyme.

A cellulase enzyme is defined as an enzyme which is capable of degrading cellulase. The cellulase enzymes that can be utilized include those obtained from *Aspergillus niger* or *Trichoderma reesei*. *Trichoderma reesei* is also referred to as *Trichoderma viride*. Although the use of a cellulase enzyme from a fungal source is preferred, the invention is not, however, to be limited by the source of the cellulase enzyme. A hemicellulase enzyme is defined as an enzyme which is capable of hydrolyzing specific types of hexosans and pentosans, including more or less complex mannans, galactans and xylans. A hemicellulase enzyme that can be utilized includes the hemicellulase enzyme obtained from *Aspergillus niger*. Notwithstanding that the use of a hemicellulase enzyme from a fungal source is preferred, the invention is not, however, to be limited by the source of the hemicellulase enzyme. Although both the cellulase and hemicellulase enzymes can be obtained by culturing an organism, then extracting and purifying the enzyme by known and conventional techniques, the applicant has found it more efficient to purchase the cellulase and hemicellulase fungal enzymes from any one of the following sources: Bio-Cat, Inc., Industrial Drive, Louisa, Va. 23093; Amano International Enzyme Company, Inc., 250 East Zion Crossroads, Troy, Va, 22974.

The beta-fructofuranosidase enzyme, cellulase enzyme and hemicellulase enzyme may be used, in accordance with the subject invention, in the following concentrations: for the beta-fructofuranosidase enzyme, a concentration of at least 25,500 Sumner units per gram of the composition; for the cellulase enzyme, a concentration of at least 12,000 FPU (Filter paper units) per gram of the composition; and for the hemicellulase enzyme, a concentration of at least 250 HCU (Hemicellulase units) per gram of composition. The amount of enzyme is not critical. However, for reasons of economics, an excessive quantity of enzyme should be avoided, and for reasons of utility, at least the minimum amount to produce satisfactory results should be used.

In another embodiment of this invention, the beta-fructofuranosidase enzyme food supplement composition includes a beta-fructofuranosidase enzyme, a cellulase enzyme, a hemicellulase enzyme, a lipase enzyme and an acid protease enzyme.

The beta-fructofuranosidase enzyme, cellulase enzyme and hemicellulase enzyme of this embodiment are as defined above. The lipase enzyme is defined as an enzyme which is capable of hydrolyzing lipids. The lipase enzyme that is preferred is obtained from *Aspergillus niger*. Although the use of a lipase enzyme from the fungal source *Aspergillus niger* is preferred, the invention is not, however, to be limited by the source of the lipase enzyme. Although the lipase enzyme can be obtained by culturing the *Aspergillus niger* organism, then extracting and purifying the enzyme by known and conventional techniques, the applicant has found it more efficient to purchase the lipase enzyme from any one of the following sources: Bio-Cat, Inc., Industrial Drive, Louisa, Va. 23093; Amano International Enzyme Company, Inc., 250 East Zion Crossroads, Troy, Va. 22974.

An acid protease enzyme is defined as an enzyme, which is capable of breaking down proteins and their degradation products, polypeptides and peptides, by hydrolysis, and is active in a pH environment ranging from a pH of 2 to a pH of 8, with the optimum pH being around 6. The acid protease enzymes that can be utilized include those obtained from *Rhizopus niveus* and *Aspergillus niger* var. *macrosporus*. Although the enzyme can be obtained by culturing the above-mentioned organisms, then extracting and purifying the enzyme by known and conventional techniques, the applicant has found it more efficient to purchase the acid protease enzyme from any one of the following sources: Bio-Cat, Inc., Industrial Drive, Louisa, Va. 23093; Amano International Enzyme Company, Inc., 250 East Zion Crossroads, Troy, Va. 22974. The invention is not, however, to be limited by the source of the lipase enzyme.

The beta-fructofuranosidase enzyme, cellulase enzyme, hemicellulase enzyme, lipase enzyme and acid protease enzyme may be used, in accordance with this embodiment of the subject invention, in the following concentrations: for the beta-fructofuranosidase enzyme, a concentration of at least 25,500 Sumner units per gram of the composition; for the cellulase enzyme, a concentration of at least 12,000 FPU (Filter paper units) per gram of the composition; for the hemicellulase enzyme, a concentration of at least 250 HCU (Hemicellulase units) per gram of composition; for the lipase enzyme, a concentration of at least 750 FIP units per gram of composition; and for the acid protease enzyme, a concentration of at least 500 Acid protease units per gram of composition. The amount of enzyme is not critical. However, for reasons of economics, an excessive quantity of enzyme should be avoided, and for reasons of utility, at least the minimum amount to produce satisfactory results should be used.

Another ingredient which is commonly added, although not essential, to the enzyme food supplement compositions of the present invention is a carrier material. Suitable carrier materials include potato starch, maltodextrins, modified starches, direct compression tablet excipients such as dicalcium phosphate, calcium sulfate and sucrose. A particularly preferred carrier ingredient is the 10 DE Maltrin M100 maltodextrin from Grain Processing Corporation. Carriers can be added in concentrations ranging from 50 to 95 weight percent of the total composition.

Various other additives which are conventionally added to enzyme food supplement compositions, such as preservatives and the like, may be utilized.

The beta-fructofuranosidase enzyme food supplement composition of the present invention was designed for use as a tablet, capsule or powder food supplement, to be taken with foods containing oligosaccharides.

One method of ingredient incorporation for the beta-fructofuranosidase enzyme food supplement compositions, in accordance with this invention, and as used to formulate the examples is as follows:

EXAMPLES

In one embodiment, a typical beta-fructofuranosidase enzyme food supplement composition of the present invention comprises the following ingredients: (1) 5.0 weight percent of beta-fructofuranosidase (ex *Saccharomyces cerevisiae*) containing approximately 85,000 Sumner units per gram of beta-fructofuranosidase obtained from Bio-Cat, Inc.; (2) 5.0 weight percent of cellulase (ex *Trichoderma viride (reesei)*) containing approximately 24,000 FPU per gram of cellulase enzyme obtained from Bio-Cat, Inc.; and (3) 5.0 weight percent of hemicellulase (ex *Aspergillus niger*) containing approximately 500 HCU per gram of hemicellulase enzyme, also obtained from Bio-Cat, Inc. The remainder of the composition consists of 85.0 weight percent of potato starch. The weight percents are weight percentages of the total composition. The 85,000 Sumner units per gram for the beta-fructofuranosidase enzyme, the 24,000 FPU per gram for the cellulase enzyme, and the 500 HCU per gram for the hemicellulase enzyme are standard units of enzyme activity per gram of individual enzyme, as explained in more detail below.

In another embodiment, a typical beta-fructofuranosidase enzyme food supplement composition of the present invention comprises the following ingredients: (1) 60.0 weight percent of beta-fructofuranosidase (ex *Saccharomyces cerevisiae*) containing approximately 85,000 Sumner units per gram of beta-fructofuranosidase enzyme obtained from Bio-Cat, Inc.; (2) 10.0 weight percent of cellulase (ex *Trichoderma viride (reesei)*) containing approximately 240,000 FPU per gram of cellulase enzyme obtained from Bio-Cat, Inc.; (3) 10.0 weight percent of hemicellulase (ex *Aspergillus niger*) containing approximately 5,000 HCU per gram of hemicellulase enzyme, also obtained from Bio-Cat, Inc.; (4) 15.0 weight percent of lipase (ex *Aspergillus niger*) containing approximately 100,000 FIP units per gram of lipase, also obtained from Bio-Cat, Inc.; and (5) 5.0 weight percent of acid protease (ex *Aspergillus niger* var. *macrosporus*) containing approximately 20,000 Acid protease units per gram of acid protease enzyme, also obtained from Bio-Cat, Inc. The weight percents are weight percentages of the total composition. The 85,000 Sumner units per gram for the beta-fructofuranosidase, the 240,000 FPU per gram for the cellulase enzyme, the 5,000 HCU per gram for the hemicellulase enzyme, the 100,000 FIP units per gram for the lipase enzyme, and the 20,000 Acid protease units per gram for the acid protease enzyme are standard units of enzyme activity per gram of individual enzyme as explained below. The total enzyme activity per gram of this particular embodiment of the invention described in the above example is as follows: beta-fructofuranosidase invertase enzyme: 51,000 Sumner u/gram; cellulase enzyme: 24,000 FPU/gram; hemicellulase enzyme: 500 HCU/gram; lipase enzyme: 15,000 FIP u/gram; and acid protease enzyme: 1,000 u/gram.

A Sumner unit is defined as that quantity of enzyme required, under standard conditions, which forms 1 mg of invert sugar from 325 mg of sucrose in 5 minutes at 25° C. An invertase enzyme breaks down sucrose with the formation of invert sugar. The formation of invert sugar under standard conditions is determined with dinitrosalicylic acid-phenol reagent. A FPU unit (Filter Paper Unit) is defined as that quantity of enzyme required, under the conditions of the assay stated in Ghose, T. K., Measurement of Cellulase Activity, IUFAC Commission on Biotechnology (1984). The cellulase in the sample hydrolyzes the substrate which is filter paper, and the reducing sugars thus released are assayed spectrophotometrically using dinitrosalicylic acid. An HCU unit (Hemicellulase Unit) is that activity that will produce a relative fluidity change of 1 over a period of five minutes in a defined locust bean gum substrate under the conditions specified in the assay stated in the above-referenced texts, section *Hemicellulase Activity*, pp. 490–491. The assay is based on the enzymatic hydrolysis of the interior glucosidic bonds of a defined locust bean gum substrate at pH 4.5 and 40° C. The corresponding reduction in substrate viscosity is determined with a calibrated viscometer. One FIP unit of enzyme activity is the amount contained in a standard preparation which liberates one microequivalent of fatty acid per minute under the conditions of the assay. Pharmaceutical Enzymes, Microbial Lipases, § 8, pp. 210–213. The specific activity is expressed in international FIP units per mg of enzyme preparation. One unit of Acid protease activity is defined as the quantity of the enzyme to produce amino acids equivalent to 100 units of tyrosine in 1 ml of filtrate per 60 minutes at 37° C.

In order to make a beta-fructofuranosidase enzyme food supplement composition in accordance with this invention, the purified enzymes, which were purchased from Bio-Cat, Inc., were dry-blended until a uniform mixture was obtained.

The present enzyme food supplement composition is ingested in the same manner as any food product and preferably taken immediately after or during ingestion of the food containing the oligosaccharides raffinose, stachyose and verbascose.

The beta-fructofuranosidase enzyme food supplement compositions of the present invention may be illustrated by way of the above examples which is presented for illustration and not intended to be limiting to the scope of the invention. The invention is not to be limited except as set forth in the following claims.

What is claimed is:

1. An enzyme food supplement composition, which alleviates gastrointestinal distress caused by ingested food containing oligosaccharides, said composition comprising at least about 25,000 Sumner units per gram of said composition of a beta-fructofuranosidase, at least about 12,000 Filter Paper Units per gram of said composition of a cellulase and at least about 250 Hemicellulase Units per gram of said composition of a hemicellulase.

2. The composition of claim 1, wherein the beta-fructofuranosidase is obtained from *Saccharomyces cerevisiae*.

3. The composition of claim 1, wherein the cellulase is obtained from a member selected from the group consisting of *Aspergillus niger* and *Trichoderma viride (reesei)*.

4. The composition of claim 1, wherein the hemicellulase is obtained from *Aspergillus niger*.

5. An enzyme food supplement composition, which alleviates gastrointestinal distress caused by ingested food containing oligosaccharides, said composition comprising at least about 25,000 Sumner units per gram of said composition of a beta-fructofuranosidase, at least about 12,000 Filter Paper Units per gram of said composition of a cellulase, at least about 250 Hemicellulase Units per gram of said composition of a hemicellulase, at least about 750 FIP units per gram of said composition of a lipase and at least about 500 Acid protease units per gram of said composition of an acid protease.

6. The composition of claim 5, wherein the beta-fructofuranosidase is obtained from *Saccharomyces cerevisiae*.

7. The composition of claim 5, wherein the cellulase is obtained from a member selected from the group consisting of *Aspergillus niger* and *Trichoderma viride* (*reesei*).

8. The composition of claim 5, wherein the hemicellulase is obtained from *Aspergillus niger*.

9. The composition of claim 5, wherein the lipase is obtained from *Aspergillus niger*.

10. The composition of claim 5, wherein the acid protease is obtained from a member selected from the group consisting of *Aspergillus niger* var. *macrosporus* and *Rhizopus niveus*.

* * * * *